United States Patent [19]

Rutherford

[11] Patent Number: 5,625,148
[45] Date of Patent: Apr. 29, 1997

[54] ULTRASONIC SCANNING HEAD AND METHOD

[75] Inventor: Jerry Rutherford, Anaheim, Calif.

[73] Assignee: Rohrback Cosasco Systems, Inc., Santa Fe Springs, Calif.

[21] Appl. No.: 428,546

[22] Filed: Apr. 25, 1995

[51] Int. Cl.$^6$ .................................................. G01N 29/04
[52] U.S. Cl. ...................................... 73/618; 73/635
[58] Field of Search ........................... 73/618, 621, 622, 73/623, 633, 634, 635, 637, 638, 639, 640, 644; 128/660.08, 660.09, 660.1, 662.03

[56] References Cited

U.S. PATENT DOCUMENTS

| | | | |
|---|---|---|---|
| 3,616,684 | 11/1971 | Nusbickel, Jr. | 73/71.5 |
| 3,958,451 | 5/1976 | Richardson | 73/67.8 |
| 4,096,757 | 6/1978 | Ishii et al. | 73/623 |
| 4,149,419 | 4/1979 | Connell, Jr. et al. | 73/621 |
| 4,341,120 | 7/1982 | Anderson | 73/618 |
| 4,515,017 | 5/1985 | McConaghy | 73/618 |
| 4,625,557 | 12/1986 | Rutherford | 73/635 |
| 4,664,121 | 5/1987 | Sanghvi et al. | 73/634 |
| 4,773,426 | 9/1988 | Molnar et al. | 73/633 |
| 4,977,898 | 12/1990 | Schwarzschild et al. | 73/623 |
| 5,025,215 | 6/1991 | Pirl | 324/220 |
| 5,031,458 | 7/1991 | Young et al. | 73/618 |
| 5,505,089 | 4/1996 | Weigel | 73/635 |

*Primary Examiner*—Hezron E. Williams
*Assistant Examiner*—Helen C. Kwok
*Attorney, Agent, or Firm*—Renner, Otto, Boisselle, Sklar

[57] ABSTRACT

A acoustical imaging scanning head includes a roller driven optical encoder. The encoder and its shaft are isolated in a non-magnetic housing. The encoder shaft and a roller driven drive shaft are provided with permanent magnets on facing steel discs on opposite sides of a relatively thin wall of a non-magnetic housing. The encoder is sealed in a chamber in such housing and is totally isolated from the surrounding environment, including the drive shaft. The position and arrangement of the magnets maintains the ability to rotate the encoder shaft to produce electrical pulses proportional to the encoder shaft rotation.

22 Claims, 1 Drawing Sheet

ULTRASONIC SCANNING HEAD AND METHOD

DISCLOSURE

This invention relates generally as indicated to an ultrasonic scanning head, and more particularly to a portable scanning head which includes an encoder driven by movement of the scanning head over a surface being tested, and a method of making and using the scanning head.

BACKGROUND OF THE INVENTION

Ultrasonic scanning heads are used in the measuring and testing of metal structures. The scanning heads are relatively small and may be hand held and include a transducer and one or more rollers, rolling over the surface being tested. A scanning head and acoustical imaging system useful in imaging thickness and defects in structures such as tanks or pipelines is shown in Rutherford U.S. Pat. No. 4,625,557. In order to limit the acoustical impedance of air, the area between the transducer and the metal surface being tested or imaged is flooded with a couplant. An example of such a system is shown in copending application of Larry A. Weigel, Ser. No. 08/317,348, filed Oct. 4, 1994 and entitled "Scanner Head Assembly And Couplant System Therefor". This makes the work site wet and messy, for example. Also, the work is often done outdoors or in less than ideal environments. Acoustical imaging underwater is very effective with the systems described, except for one major problem.

The optical encoder driven by the roller is sensitive to the environment, and underwater or in other deleterious environments, the optical encoder tends to fail. Optical encoders are not what could be considered spare parts which would be handy at the test site. Even if readily available, they are not easy to replace. Failure of the encoder brings the entire project to a halt until a new one can be shipped and the failed one replaced.

Environmentally isolated optical encoders are not commercially available. Attempts to encase the encoder with the drive shaft projecting from the encasement and sealed to prevent water ingress have been less than satisfactory. Even the best of rotating seals tends to fail due to the severe environmental conditions encountered, particularly in underwater work. Such work encounters salt, sand, grit and general junk, for example, all of which adversely affects rotating seals. With the encoder encased or encapsulated, the failed encoder resulting from a failed seal is even more difficult to repair or replace.

It would, accordingly, be desirable to have a scanning head with an encoder which is completely physically isolated from its environment including its drive means, so that there are no wear sensitive points or areas which might permit environmental ingress to the encoder.

SUMMARY OF THE INVENTION

A scanning head for acoustical imaging of metal structures is adapted to move over the surface of the structure being analyzed. A roller on the scanning head drives an optical encoder which provides distance increment signals and drives the ultrasonic transceiver and display circuitry. The encoder and its rotating shaft are completely physically isolated, not only from the environment, but also from the roller driven drive means on the scanning head. The encoder, including its rotating shaft, is mounted in a chamber in a non-magnetic housing, and the chamber is sealed with a potting compound completely isolating the encoder and its rotating shaft from the environment.

The rotating shaft of the encoder projects into a subchamber and includes a disc having permanent magnets mounted thereon. The disc and magnets face a relatively thin barrier wall of the non-magnetic housing. On the opposite side of the wall is a closed chamber. A drive shaft is journalled for rotation on the scanning head frame and projects into such closed chamber in axial alignment with the shaft of the encoder. The drive shaft also has a disc and magnets facing the wall so that the magnets create magnetic flux lines extending through the non-magnetic wall magnetically to couple the drive shaft to the encoder shaft through the housing wall. The drive shaft is driven through a drive belt from the roller.

The magnets are preferably rare earth magnets and mounted in steel discs. The magnets are mounted on the discs equally circumferentially spaced with alternate magnets having opposite poles revealed or facing the thin non-magnetic wall of the housing. The magnets and disc on the nonisolated side of the wall may be covered with a special protective coating. In the event of a bearing or other failure, for example, the external side of the magnetic drive can quickly be replaced. The invention totally isolates the optical encoder from the surrounding environment while fully maintaining the ability to rotate the encoder shaft to produce pulses proportional to shaft rotation. The invention also includes the method of use and construction of the scanning head assembly.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

DESCRIPTION OF THE PREFERRED EMBODIMENT

Figure 1:
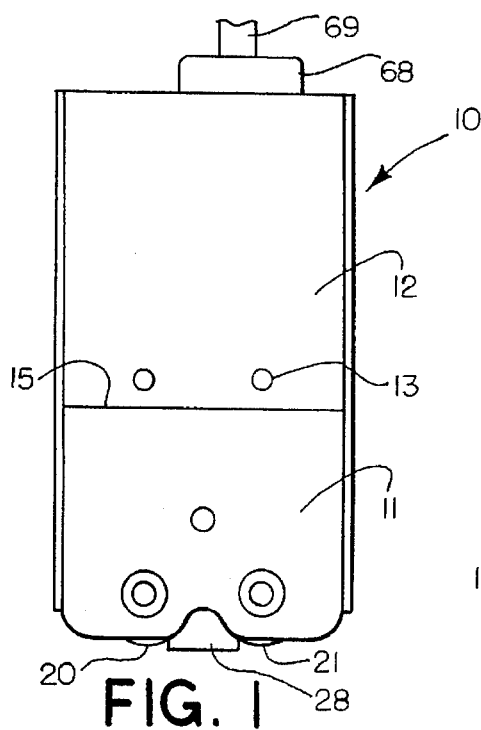
FIG. 1 is a side elevation of a hand held scanning head in accordance with the invention.
Figure 2:
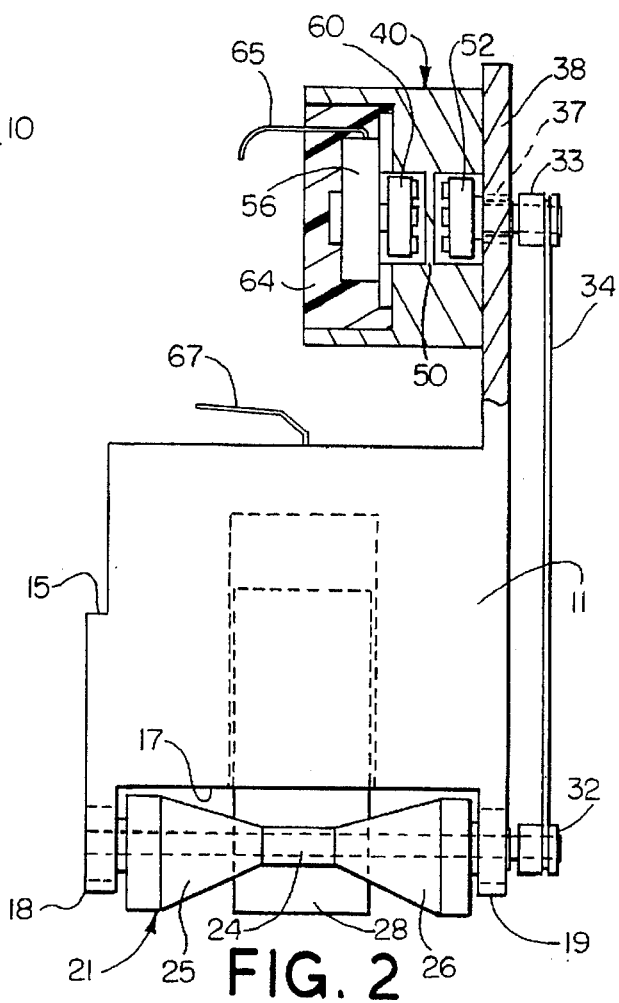
FIG. 2 is an enlarged elevation partially broken away and in section with the shroud or cover removed as seen from the right hand side of FIG. 1.
Figure 3:
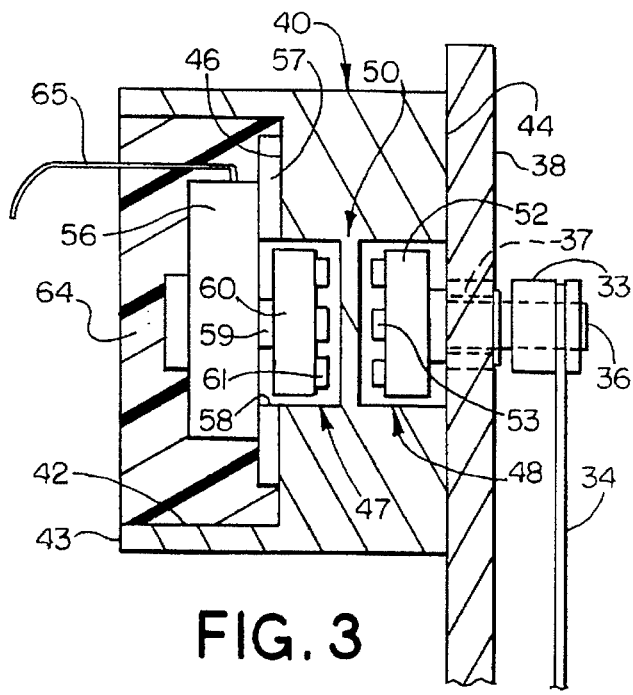
FIG. 3 is an enlarged section of the magnetic drive coupling.

Referring initially to FIGS. 1, 2 and 3, there is illustrated a scanning head shown generally at 10 which includes a scanhead body or main frame 11, and a shroud 12 which is secured to the main frame by fasteners 13. The lower end of the wall of the shroud facing the viewer in FIG. 1 seats on shoulder 15 seen more clearly in FIG. 2.

The main frame 11 may comprise a machined block of aluminum alloy, for example, which along its lower end includes a channel 17 forming depending side plates 18 and 19, between which rollers 20 and 21 are journalled. Each roller has a relatively small central diameter indicated at 24 with opposed conical sections seen at 25 and 26. This enables the scanning head to move over curved surfaces such as the profile of a pipe.

A transducer 28 projects downwardly from the frame 11 between such rollers and is nested closely between the opposite conical surfaces. The transducer is mounted for vertical movement. Such vertical movement is limited by a set screw or stop screw, and the transducer is urged downwardly by one or more compression springs, not shown.

The axle of roller 21 also drives pulley 32 on the exterior of the frame 11. The pulley 32 drives another pulley 33 through belt 34 in a one-two-one ratio. The pulley 33 is mounted on shaft 36, journalled at 37 in upstanding plate 38 which is part of the frame 11.

Mounted on the opposite side of the plate 38 from the pulley 33 is an encoder housing shown generally at 40. The encoder housing is machined from a non-magnetic block of metal such as an aluminum alloy and includes an encoder chamber 42 opening to one side 43 of the housing. The opposite side 44 is mounted on the plate 38. The chamber 42 includes a shoulder 46, and a smaller subchamber or second chamber extends beyond the shoulder as seen at 47. A similar smaller chamber 48 opening to the opposite side 44 of the housing is aligned with the chamber 47 but separated therefrom by a relatively thin barrier wall 50. Accordingly, the chambers 42, 47 in one face or side of the housing block are separated from the chamber 48 in the opposite face by the relatively thin non-magnetic barrier wall 50.

Mounted on the end of shaft 36 within the chamber 48 is a steel disc 52. In the circular face of the disc 52 facing the barrier wall 50, there is mounted a number of equally circumferentially spaced permanent magnets 53.

The optical encoder 56 may be mounted on a mounting plate such as plate 57 which includes a hole 58 aligned with the subchamber 47. The plate and the optical encoder are mounted on the shoulder 46 between the larger chamber 42 and the subchamber 47. The optical encoder includes a short shaft 59 projecting through the hole 58 into the chamber 47. On such shaft is mounted disc 60, the face of which is provided permanent magnets 61 facing the barrier wall 50.

When the optical encoder is installed in the chamber 42, and before the housing is mounted on the plate 38 of the frame 11, the entire chamber 42 is filled with a potting compound seen at 64. The plate keeps the potting compound out of the chamber 47 and away from the shaft 59. The encoder wiring exits the potting compound as seen at 65. In this manner, the optical encoder is totally isolated from its environment even including its drive shaft 36. The potting compound may, for example, be an epoxy.

The wiring 65, together with the wiring from the transducer seen at 67, passes through strain relief 68 at the top of the shroud 12 and exits at 69 to the imaging system such as shown in prior Rutherford U.S. Pat. No. 4,625,557.

Figure 4:
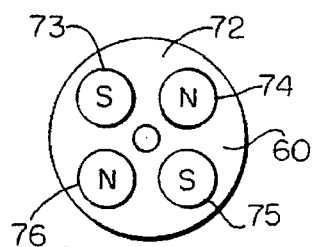
FIG. 4 is an axial view of a disc showing the arrangement of the magnets.
Figure 5:
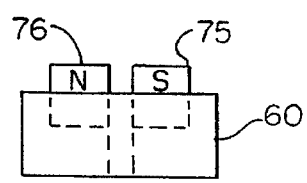
FIG. 5 is a transaxial view of the disc of FIG. 4.
Figure 6:
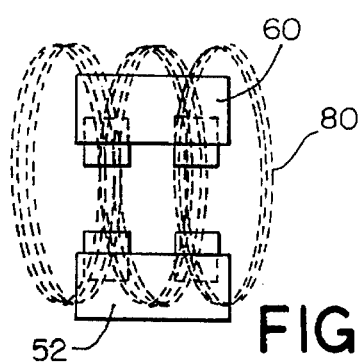
FIG. 6 is a schematic illustration of the two discs and the magnetic flux lines created.

Referring now to FIGS. 4, 5 and 6, it will be seen that the discs 60 or 52 include a circular face 72 which faces the barrier wall and in such face the permanent magnets seen at 73, 74, 75 and 76 are mounted. The magnets are mounted so that alternate magnets circumferentially have alternate poles facing the barrier wall. Thus, the magnets 73 and 75 have the south poles facing the barrier walls while the diametrically opposite magnets 76 and 74 have the north poles facing such wall. While FIGS. 4 and 5 show four magnets circumferentially equally arranged in a ring or circle, it will be appreciated that the discs and magnet ring or circle may accommodate more magnets as long as they are of an even number and the diameter of the discs may vary to vary the torque transmitted.

The discs 52 and 60 are made of steel or other ferrous metal and such discs actually focus and strengthen the magnetic flux lines created by the magnets and also act as a magnet saver. It is preferred to use rare earth disc magnets such as neobinium-iron-boron. The magnetic discs are mounted in machined recesses in the steel discs and may be held in place by an adhesive. The magnetic flux lines seen generally at 80 in FIG. 6 will automatically align and attempt to maintain that alignment when one disc is rotated with respect to the other. The magnetic couplings illustrated can produce torsional forces sufficient to rotate the optical encoder shaft without direct mechanical connections, and this enables the placing of the optical encoder and the attached magnetic disc in a potted chamber, totally isolating the encoder from the surrounding environment while maintaining the ability to rotate the encoder shaft and produce electrical pulses proportional to the shaft rotation.

Once installed in the isolation chamber, the encoder and magnetic disc are virtually impervious to external conditions. However, the steel disc and magnets in the chamber 48, even though shaft sealed from the environment, may be covered with a suitable protective coating such as a Paralene to act as a shield. In any event, replacement of the external set in chamber 48 is relatively a simple matter. If the optical encoder is ever replaced, it would normally be replaced housing and all.

It can now been seen that there is provided an improved optical encoder and method of using and making that encoder for use in adverse environments and particularly for use underwater.

Although the invention has been shown and described with respect to certain preferred embodiments, it is obvious that equivalent alterations and modifications will occur to others skilled in the art upon the reading and understanding of this specification. The present invention includes all such equivalent alterations and modifications, and is limited only by the scope of the claims.

What is claimed is:

1. A scanning head for ultrasonic testing of metal structures comprising a scanhead body adapted to move over the surface of the structure being scanned, an encoder operative to create an image in relation to the position of the scanhead body, drive means to drive the encoder as said scanhead body moves, and barrier wall means to isolate and seal the encoder from the environment of said drive means.

2. A scanning head as set forth in claim 1 wherein said encoder includes driven means driving said encoder operative in response to said drive means, a housing for said encoder, said housing including said barrier wall means to separate said drive means from said driven means.

3. A scanning head as set forth in claim 2 including a chamber in said housing for said encoder, said encoder being mounted in said chamber so that said driven means faces said barrier wall means.

4. A scanning head as set forth in claim 3 wherein said wall has an opposite side and including a second chamber in said housing for said drive means, said drive means being mounted in said second chamber so that said drive means faces said opposite side of the barrier wall means as said driven means.

5. A scanning head as set forth in claim 3 wherein said encoder is encapsulated in said chamber.

6. A scanning head as set forth in claim 3 wherein said chamber is filled with a potting compound to seal said encoder therein.

7. A scanning head as set forth in claim 2 wherein said drive means and driven means are magnetic and said barrier wall means is substantially non-magnetizable.

8. A scanning head as set forth in claim 7 wherein each of said drive and driven means comprises a rotatable disc substantially axially aligned on opposite sides of said barrier wall means.

9. A scanning head as set forth in claim 8 including permanent magnets arranged circumferentially around each disc.

10. A scanning head as set forth in claim 9 wherein said magnets include poles which are arranged around each said disc with the poles parallel to the axis of the respective disc and with alternate magnets having alternate poles facing the barrier wall means.

11. A scanning head as set forth in claim 1 wherein said scanning head has at least one roller engaging the surface of the structure being scanned, said roller driving said drive means.

12. A scanning head as set forth in claim 11 including a one-to-one drive ratio between said roller and said drive means.

13. A method of ultrasonic testing of metal structures in adverse environments comprising the step of providing a scanhead which includes an encoder, moving the scanhead to drive the encoder to create an image in relation to the position of the scanhead, and environmentally isolating the encoder and all moving parts of said encode from the environments in which the scanhead is working.

14. A method as set forth in claim 13 including the step of providing the encoder with a drive transmission including a drive part and a driven part, and providing a barrier wall between said drive and driven parts.

15. A method as set forth in claim 14 wherein said drive and driven parts are magnetic and said barrier wall is substantially non-magnetizable.

16. A method as set forth in claim 15 wherein the drive and driven parts are discs of ferrous material.

17. A method as set forth in claim 16 including the step of arranging permanent magnets circumferentially around said discs.

18. A method as set forth in claim 17 including the step of arranging the magnets for each of said discs to have alternate poles facing the barrier wall.

19. A method as set forth in claim 18 including the step of placing the drive and driven parts in two separate chambers in a housing, said barrier wall separating said chambers.

20. A method as set forth in claim 19 including the step of encapsulating the encoder and said driven part in one of said chambers.

21. A method as set forth in claim 20 including the step of filling said one of said chambers with potting compound to encapsulate said encoder.

22. A method as set forth in claim 19 including the step of machining said housing from aluminum.

* * * * *